United States Patent
Uhland et al.

(10) Patent No.: US 9,017,310 B2
(45) Date of Patent: Apr. 28, 2015

(54) TRANSMUCOSAL DRUG DELIVERY DEVICE AND METHOD INCLUDING MICRONEEDLES

(75) Inventors: Scott Uhland, San Jose, CA (US); Eric Peeters, Mountain View, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 920 days.

(21) Appl. No.: 12/576,075

(22) Filed: Oct. 8, 2009

(65) Prior Publication Data

US 2011/0087195 A1    Apr. 14, 2011

(51) Int. Cl.
*A61K 9/22* (2006.01)
*A61M 37/00* (2006.01)

(52) U.S. Cl.
CPC ... *A61M 37/0015* (2013.01); *A61M 2037/0023* (2013.01)

(58) Field of Classification Search
USPC ............... 604/890.1, 891.1, 20–22, 264, 272, 604/239, 506, 48, 514, 515, 93.01, 285
See application file for complete search history.

(56) References Cited

U.S. PATENT DOCUMENTS

| | | |
|---|---|---|
| 4,304,232 A | 12/1981 | Michaels |
| 4,308,867 A | 1/1982 | Roseman et al. |
| 4,402,695 A | 9/1983 | Wong |
| 4,687,423 A | 8/1987 | Maget et al. |
| 4,886,514 A | 12/1989 | Maget |
| 4,902,278 A | 2/1990 | Maget et al. |
| 5,002,540 A | 3/1991 | Brodman et al. |
| 5,062,834 A | 11/1991 | Gross et al. |
| 5,090,963 A | 2/1992 | Gross et al. |
| 5,112,614 A | 5/1992 | Magruder et al. |
| 5,135,499 A | 8/1992 | Tafani et al. |
| 5,318,557 A | 6/1994 | Gross |
| 5,354,264 A | 10/1994 | Bae et al. |

(Continued)

FOREIGN PATENT DOCUMENTS

| | | |
|---|---|---|
| DE | 4130843 A1 | 3/1993 |
| WO | 94/01165 A1 | 1/1994 |

(Continued)

OTHER PUBLICATIONS

Hashimoto, et al. (2008). "Oxidative stress induces gastric epithelial permeability through claudin-3." Biochemical and Biophysical Research Communications. Retrieved from http://www.elsevier.com//locate/ybbrc. (5 pages).

(Continued)

*Primary Examiner* — Aarti B Berdichevsky
*Assistant Examiner* — Laura Schell
(74) *Attorney, Agent, or Firm* — Sutherland Asbill & Brennan LLP

(57) ABSTRACT

Devices and methods for transmucosal drug delivery are provided. A device includes a housing configured for intralumenal deployment into a human or animal subject; a drug-dispensing portion which contains at least one drug; and a plurality of microneedles extending, or being extendable from, the housing, the plurality of microneedles being configured to disrupt at least one region of a mucosal barrier adjacent the housing at a selected time after being intralumenally deployed in the human or animal subject. The device is operable to dispense the drug from the housing to a region of the mucosal barrier disrupted by the plurality of microneedles.

25 Claims, 3 Drawing Sheets

(56) References Cited

U.S. PATENT DOCUMENTS

| | | | |
|---|---|---|---|
| 5,415,629 | A | 5/1995 | Henley |
| 5,522,804 | A | 6/1996 | Lynn |
| 5,593,552 | A | 1/1997 | Joshi et al. |
| 5,780,058 | A | 7/1998 | Wong et al. |
| 5,816,248 | A | 10/1998 | Anderson et al. |
| 5,928,195 | A | 7/1999 | Malamud et al. |
| 6,030,375 | A | 2/2000 | Anderson et al. |
| 6,086,909 | A | 7/2000 | Harrison et al. |
| 6,139,538 | A | 10/2000 | Houghton et al. |
| 6,183,434 | B1 | 2/2001 | Eppstein |
| 6,322,532 | B1 | 11/2001 | D'Sa et al. |
| 6,352,524 | B1 | 3/2002 | Bunt et al. |
| 6,423,039 | B1 | 7/2002 | Rathbone et al. |
| 6,444,224 | B1 | 9/2002 | Rathbone et al. |
| 6,450,991 | B1 | 9/2002 | Bunt et al. |
| 6,532,386 | B2 | 3/2003 | Sun et al. |
| 6,591,133 | B1 | 7/2003 | Joshi |
| 6,638,246 | B1* | 10/2003 | Naimark et al. ............ 604/103 |
| 6,743,211 | B1* | 6/2004 | Prausnitz et al. ............ 604/239 |
| 6,756,053 | B2 | 6/2004 | Zhang et al. |
| 6,776,164 | B2 | 8/2004 | Bunt et al. |
| 6,805,877 | B2 | 10/2004 | Massara et al. |
| 6,835,392 | B2 | 12/2004 | Hsu et al. |
| 6,978,172 | B2 | 12/2005 | Mori et al. |
| 7,004,171 | B2 | 2/2006 | Benita et al. |
| 7,083,590 | B1 | 8/2006 | Bunt et al. |
| 7,486,989 | B2 | 2/2009 | Sun et al. |
| 7,497,855 | B2 | 3/2009 | Ausiello et al. |
| 7,732,408 | B2 | 6/2010 | Josephson et al. |
| 2002/0010414 | A1 | 1/2002 | Coston et al. |
| 2003/0018295 | A1 | 1/2003 | Henley et al. |
| 2003/0130558 | A1 | 7/2003 | Massara et al. |
| 2003/0219472 | A1 | 11/2003 | Paulelli et al. |
| 2004/0059388 | A1 | 3/2004 | Herbst et al. |
| 2004/0082937 | A1 | 4/2004 | Ausiello et al. |
| 2004/0087893 | A1 | 5/2004 | Kwon |
| 2004/0219192 | A1 | 11/2004 | Horstmann et al. |
| 2005/0054969 | A1 | 3/2005 | Hoff et al. |
| 2005/0124875 | A1 | 6/2005 | Kawano et al. |
| 2005/0244502 | A1 | 11/2005 | Mathias et al. |
| 2005/0267440 | A1 | 12/2005 | Herman et al. |
| 2006/0024358 | A1 | 2/2006 | Santini et al. |
| 2006/0184092 | A1* | 8/2006 | Atanasoska et al. ............ 604/20 |
| 2007/0038181 | A1* | 2/2007 | Melamud et al. ............ 604/158 |
| 2007/0225634 | A1 | 9/2007 | Ferren et al. |
| 2007/0269385 | A1* | 11/2007 | Yun et al. ............ 424/45 |
| 2008/0004564 | A1 | 1/2008 | Smith |
| 2008/0004596 | A1 | 1/2008 | Yun et al. |
| 2008/0171950 | A1* | 7/2008 | Franco ............ 600/547 |
| 2008/0234546 | A1 | 9/2008 | Kawano et al. |
| 2008/0242928 | A1 | 10/2008 | Kawano et al. |
| 2008/0262412 | A1 | 10/2008 | Atanasoska et al. |
| 2008/0269666 | A1* | 10/2008 | Wang et al. ............ 604/21 |
| 2009/0131737 | A1 | 5/2009 | Ferren et al. |
| 2009/0171315 | A1 | 7/2009 | Versi |
| 2009/0306633 | A1 | 12/2009 | Trovato et al. |
| 2011/0087155 | A1 | 4/2011 | Uhland et al. |
| 2011/0087192 | A1 | 4/2011 | Uhland et al. |
| 2011/0087195 | A1 | 4/2011 | Uhland et al. |

FOREIGN PATENT DOCUMENTS

| | | |
|---|---|---|
| WO | 94/18952 A1 | 9/1994 |
| WO | 97/41831 A1 | 11/1997 |
| WO | 01/12101 A1 | 2/2001 |
| WO | 2004/000389 A2 | 12/2003 |
| WO | 2005/056708 A2 | 6/2005 |
| WO | 2005/089728 A2 | 9/2005 |
| WO | 2007/047811 A2 | 4/2007 |
| WO | 2007041119 A1 | 4/2007 |
| WO | 2007/140416 A2 | 12/2007 |
| WO | 2009/081411 A2 | 7/2009 |
| WO | 2010/048478 A2 | 4/2010 |

OTHER PUBLICATIONS

Seth, et al. (Feb. 21, 2008). "Probiotics ameliorate the hydrogen peroxide-induced epithelial barrier disruption by a PKC- and MAP kinase-dependent mechanism." Am J Physiol Gastrontest Liver Physiol. Retrieved from http://www.ajpgi.org. (10 pages).

EPO Search Report of European Patent Application No. 10187042.6 dated Mar. 3, 2011.

Bridges, et al., "Timed-Artificial Insemination in Beef Cows: What are the Options?," Purdue University Cooperative Extension Service, West Lafayette, IN, (Mar. 2008).

Sá Filho, O. G. et al., "Fixed-time artificial insemination with estradiol and progesterone for Bos indicus cows II: Strategies and factors affecting fertility," Science Direct, Theriogenology 72 (2009) 210-218.

* cited by examiner

TRANSMUCOSAL DRUG DELIVERY DEVICE
AND METHOD INCLUDING
MICRONEEDLES

FIELD

The presently disclosed embodiments relate to implantable medical devices, and more particularly to devices and methods for the transmucosal delivery of drugs to a patient.

BACKGROUND

Transmucosal drug delivery is an area of interest because of the potential of delivering systemically-acting drugs with a high relative bioavailability by avoiding first-pass metabolism effects, the potential of locally delivering therapeutic agents to a site of interest, and the convenience of the application routes. Some of the possible sites for transmucosal drug delivery include the buccal, nasal, vaginal and rectal administration routes.

There are a number of challenges associated with transmucosal drug delivery, particularly with the transmucosal delivery of macromolecules comprising certain amino acid sequences. Enzymes present in fluid secreted by the mucosal tissue degrades certain amino acids. The types of enzymes exhibited by a mucosal tissue vary depending on the location of the mucosal tissue. Enzymes present in the vaginal fluid include nucleases, lysozyme, esterase, guaiacol peroxidase, aldolase, and β-glucuronidase. In addition, aminopeptidase, β-glucuronidase, phosphatases, lactate dehydrogenase, esterases, and type 5 phosphodiesterase are bound to the apical cell layers along the surface of the vaginal mucosa. The presence of these enzymes, particularly the aminopeptidases, is one factor that reduces the bioavailability of vaginally applied protein and peptide drugs.

Other mucosal tissues exhibit other enzymes which may degrade certain drugs. For example, the gastrointestinal tract exhibits mixed function oxidase systems, alcohol dehydrogenase, monoamine oxidase, reductases, p-nitroanisole demethylase, ethoxycournarin-o-deethylase, epoxide hydrolase, UDP-glucuronyltransferase, sulfokinase, glutathione-S-transferase, glycine transferase, acetyltransferase, and calechol-O-methyltransferase. These enzymes reduce the bioavailability of protein and peptide drugs applied to such mucosal tissues.

Furthermore, most mucosal tissues continuously excrete a viscous aqueous-based liquid. This viscous liquid presents additional challenges to transmucosal drug delivery. First, the viscous liquid traps and slows down the intrusion of foreign matter, thus allowing its intrinsic enzymatic and other defense mechanisms time to degrade and/or kill the foreign body. Secondly, the viscous liquid fluid continuously cleans and washes the surface of the mucosal tissue as it is expelled from the tissue. As such, a significant amount of drug may be wasted using conventional application techniques.

In the context of vaginal drug delivery, the vaginal mucosal membrane may be viewed as two barriers in series, an aqueous barrier and the mucosal membrane barrier. The mucosal lining is a stratified squamous epithelium that is glycogenated and nonkeratinized. The human vaginal epithelium consists of approximately 25 cell layers, depending on maturity and location. Like most other stratified epithelia, the human vaginal epithelium contains a tight junction (TJ) system, located in the uppermost cell layers. These TJs separate the apical cell surface domains from the basolateral cell surface domains and provide a primary barrier to the transmucosal delivery of water-soluble species. It is these epithelia and TJs present in all mucosa of the body, not just the vagina, that impede local administration of drug.

Accordingly, it would be desirable to provide devices and methods to improve the effectiveness of transmucosal drug delivery.

SUMMARY

Devices and method for transmucosal drug delivery are provided. In one aspect, an intralumenal device is provided that includes a housing configured for intralumenal deployment into a human or animal subject; a drug-dispensing portion which contains at least one drug; and a plurality of microneedles extending, or being extendable from, the housing. The plurality of microneedles is configured to disrupt at least one region of a mucosal barrier adjacent the housing at a selected time after being intralumenally deployed in the human or animal subject. The device is operable to dispense the drug from the housing to a region of the mucosal barrier disrupted by the plurality of microneedles. In one embodiment, the housing is configured for intravaginal deployment. In one embodiment, the drug is a protein or peptide. For example, the drug may be a hormone or steroid.

In one embodiment, the device includes a receiver adapted to receive power or control signals from a transmitting device when the device is intralumenally deployed in the human or animal subject. In another embodiment, the device further includes a controller configured to actuate the release of the at least one drug from the housing after the plurality of microneedles penetrate the mucosal barrier. The device may be wirelessly powered, wirelessly controlled/operated, or both wirelessly powered and controlled/operated.

In various embodiments, the drug dispensing portion of the device includes a positive displacement element for actively dispensing the drug from the housing. The positive displacement element may be selected, for example, from a mechanical displacement element, an osmotic swelling displacement element, a gas-volume displacement element, a magnetically-induced phase transformation element, a thermally-induced phase transformation element, a piezoelectric actuator, an electrostatically-induced compression element, an actuatable dispensing valve with a static pressure head, or a combination thereof.

In one embodiment, the device further includes an actuator configured to move the plurality of microneedles from a first position to a second position in which the plurality of microneedles penetrate the mucosal barrier at the selected time. For example, the microneedles may be contained within the housing in the first position. In one embodiment, the device includes a controller configured to actuate the release of the at least one drug after the plurality of microneedles are actuated to the second position. In another case, the device further includes a dissolvable coating or a moveable covering configured to expose the microneedles at the selected time. In one embodiment, the device includes a controller configured to actuate the release of the at least one drug after the plurality of microneedles are exposed.

In another aspect, a method is provided for local transmucosal delivery of a drug to a human or animal subject. In one embodiment, the method includes deploying a drug delivery device within a mucosal tissue lumen; penetrating the mucosal tissue with a plurality of microneedles that extend from, or are extendable from, the drug delivery device at a selected time after the drug delivery device is deployed in the lumen; and dispensing from the device a drug such that the drug is delivered through the plurality of microneedles into the mucosal tissue or is delivered to the region of the mucosal tissue that is disrupted by the microneedles. In particular embodiments, the lumen comprises the vagina, uterus, or rectum of the human or animal subject.

In one embodiment of the method, the drug is dispensed from the drug delivery device via a positive displacement process. In various embodiments, the positive displacement process comprises mechanical displacement, osmotic swelling displacement, gas-volume displacement, magnetically-induced phase transformation, thermally-induced phase transformation, piezoelectric actuation, electrostatically-induced compression, static pressure head displacement through an actuatable dispensing valve, or a combination thereof.

In one embodiment, the penetrating of the mucosal tissue comprises moving a plurality of microneedles from a first position to a second position in which the plurality of microneedles penetrate the mucosal barrier. In another embodiment, the penetrating of the mucosal tissue comprises dissolving a dissolvable coating or moving a moveable covering to expose the microneedles at the selected time.

In yet another aspect, an intravaginal device is provided for transmucosal drug delivery. The device includes a housing configured for intravaginal deployment into a human or animal subject; a plurality of microneedles extending from, or extendable from, the housing configured to penetrate a region of the mucosal barrier adjacent to the housing at a selected time after being intravaginally deployed in the human or animal subject; and a drug dispenser which comprises a drug repository containing at least one drug and a positive displacement element adapted to dispense the at least one drug from the housing through plurality of microneedles or onto the region of the mucosal tissue disrupted by the microneedles. In certain embodiments, the device may further include (i) a controller configured to control the actuation of the positive displacement element, and/or (ii) an actuator configured to move the plurality of microneedles from a first position to a second position in which the plurality of microneedles penetrate the mucosal barrier at the selected time. In another embodiment, the device further includes a dissolvable coating or a moveable covering configured to expose the microneedles at the selected time.

DRAWINGS

DETAILED DESCRIPTION

A transmucosal drug delivery device is provided for intralumenal deployment. The term "intralumenal," as used herein, refers to devices which are placed within a body cavity, channel, tube, or the like, having a mucosal tissue wall. The term includes, but is not limited to, intravaginal, intrauterine, and intragastrointestinal sites. The intralumenal deployment, or placement, of the device is generally maintained for the duration of delivery of at least one or more dosages of the drug. The deployed device may be retrieved from the lumen as desired, including for example, between delivery of individual dosages, following the delivery of several doses of drug, or following completion of a course of treatment of multiple doses. The device may be deployed until the drug payload is depleted.

In some embodiments, the transmucosal drug delivery device includes (i) a housing configured to allow deployment within a lumen, (ii) one or more repositories for containing a drug, and (iii) a plurality of microneedles extending from, or being extendable from, the housing. The drug delivery device may also include an integral control module for controlling the release or delivery of the drug from the device and/or movement or penetration of the microneedles into the mucosal tissue.

In another aspect, methods are provided for transmucosal drug delivery. The method includes placing, or deploying, the drug delivery device within the lumen of a patient, or a human or animal subject. The lumen may be, for example, a vagina, cervix, uterus, or part of the gastrointestinal tract, such as the rectum.

After the drug delivery device is placed in the lumen, the microneedles of the drug delivery device may penetrate the mucosal side wall of the lumen. The drug delivery device may then dispense the drug through the microneedles into the mucosal tissue or to a region of the mucosal tissue disrupted by the microneedles. This penetration by the microneedles advantageously can enhance the drug transfer rate and/or amounts able pass undegraded through the mucosal barrier, thereby improving the effectiveness of the transmucosal administration of the drug.

The devices and methods described herein may further include one or more of the mucosal permeation enhancement features and techniques described in U.S. patent application Ser. No. 12/576,087, entitled "Transmucosal Drug Delivery Device and Method Including Chemical Permeation Enhancers" and in U.S. patent application Ser. No. 12/576,124, entitled "Transmucosal Drug Delivery Device and Method Including Electrically-Actuated Permeation Enhancer," which are filed concurrently herewith and which are incorporated by reference in their entirety.

Figure 1:
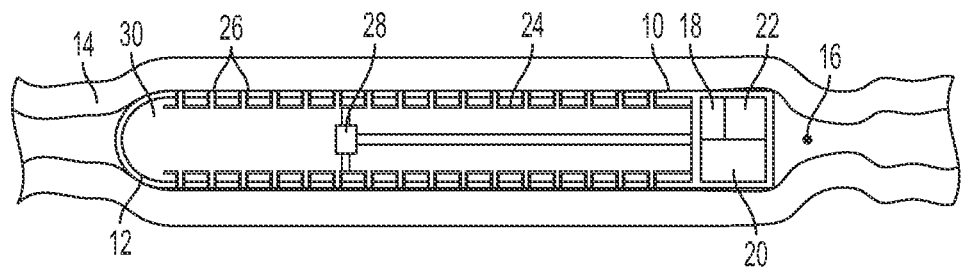
FIG. 1 is a section view, illustrating the placement of a transmucosal drug delivery device in a tissue lumen.

In some embodiments, the microneedles are actuated at a selected time to penetrate the mucosal tissue wall while the device is deployed in the lumen. For example, as illustrated in FIG. 1, a transmucosal drug delivery device 10 may be provided having a housing 12 comprising a drug repository 30 containing one or more drugs. The housing 12 may be configured for placement within a lumen 16, having a mucosal tissue 14. The housing 12 may also contain a microneedle carriage 24 having a plurality of microneedles 26 attached thereto and an actuator 28 for moving the microneedle carriage 24 and the microneedles 26 between a first position (shown in FIG. 1) to a second position (shown in FIG. 2). The housing 12 may also comprise a control module 18 for controlling the actuator 28 and/or for controlling the release of the drug from the drug repository 30.

The control module 18 includes a power source 20, such as a battery, and controller 22. The controller 22 may be configured to control the movement of the microneedle carriage 24 and microneedles 26 by controlling actuator 28 and it may control the timing and sequence of the delivery of one or more drugs. As is described in greater detail hereinafter, various mechanisms may be employed to dispense the drug from the housing via a positive displacement process or otherwise.

Figure 2:
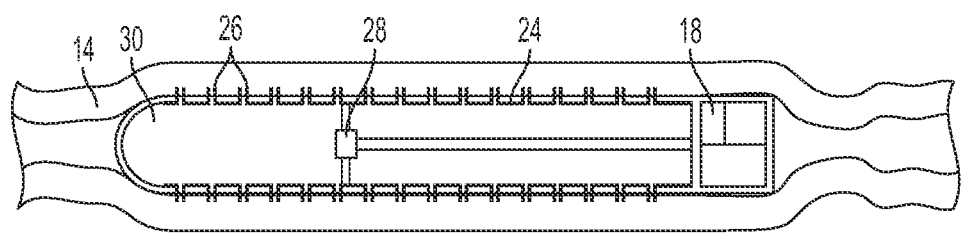
FIG. 2 is a section view, illustrating the penetration of microneedles of the device of FIG. 1 into the mucosal tissue of a lumen.

As illustrated in FIG. 2, the actuation of actuator 28 by the control module 18 may cause the microneedles 26 to extend from the housing into the mucosal tissue 14 surrounding the device. Once the microneedles 26 have penetrated the mucosal tissue 14, the control module 18 may actuate the release of the drug from the drug repository 30 or the drug may be allowed to diffuse through the mucosal tissue via the microneedles 26 or the drug may be dispensed from the device via a positive displacement process.

Figure 3:
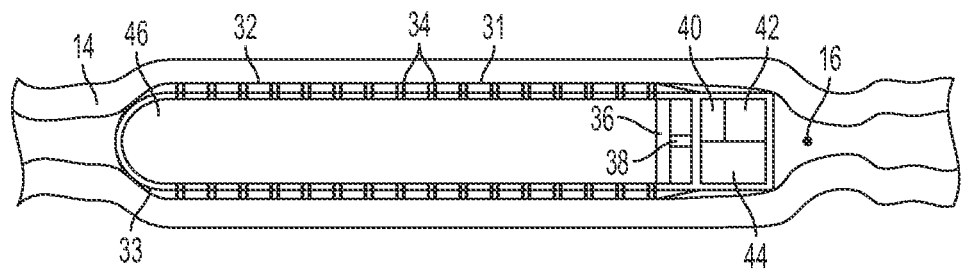
FIG. 3 is a section view, illustrating the placement of a transmucosal drug delivery device having a dissolvable coating in a lumen.

In some embodiments, static microneedles may be used in combination with a dissolvable or movable covering to allow for penetration of the mucosal tissue at a selected time. For example, as illustrated in FIG. 3, a drug delivery device 31 may be provided having a housing containing a drug repository 46, a plurality of static microneedles 34 attached to and extending away from the housing 33, and a moveable covering or a dissolvable coating 32 covering a portion of the housing 33 and at least partly surrounding the static microneedles 34. The housing 33 may also contain a piston 36, an actuator 38 for moving the piston, and a control module 40 for controlling the actuator 38.

Figure 4:
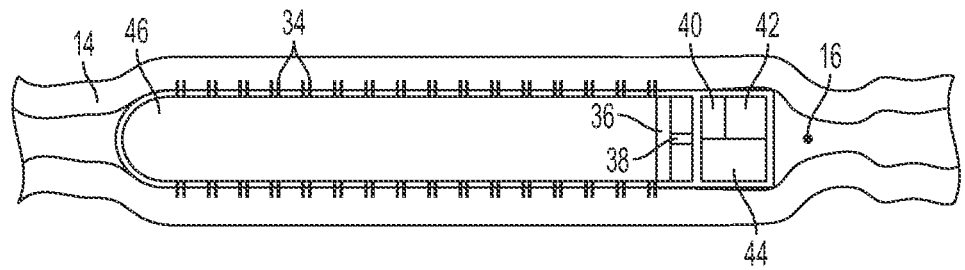
FIG. 4 is a section view, illustrating the penetration of microneedles of the device of FIG. 3 into the mucosal tissue after the dissolvable coating dissolves.
Figure 5:
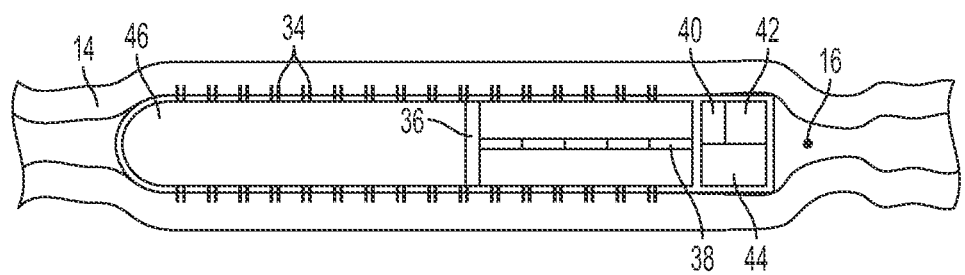
FIG. 5 is a section view, illustrating the delivery of a drug from the device of FIG. 3 into the mucosal tissue after the microneedles penetrate the mucosal tissue.

Similar to the embodiment of FIG. 1, the control module 40 of the embodiments of FIGS. 3-9, includes a power source 44, such as a battery, and controller 42. In the embodiment of FIGS. 3-5, the controller 42 may be configured to control the timing of delivery of the drug by controlling actuator 38. As is described in greater detail hereinafter, various other mechanisms may be employed to dispense the drug from the housing via a positive displacement process or otherwise.

As illustrated in FIG. 4, the static microneedles 34 may penetrate the mucosal tissue 14 after the dissolvable coating 32 dissolves. As illustrated in FIG. 5, once the static microneedles 34 have penetrated the mucosal tissue 14, the control module 40 may actuate the actuator 38 to advance the piston 36 through the drug repository 46 to dispense the drug from the drug repository 46 through the microneedles 34 into the mucosal tissue 14.

Figure 6:
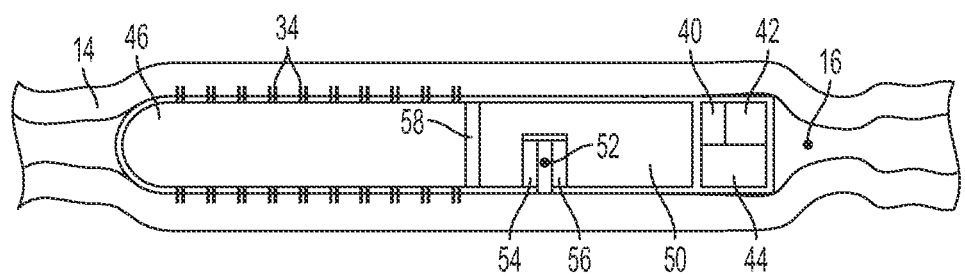
FIG. 6 is a section view, illustrating a drug delivery device having a gas-volume displacement mechanism for dispensing a drug through microneedles.
Figure 7:
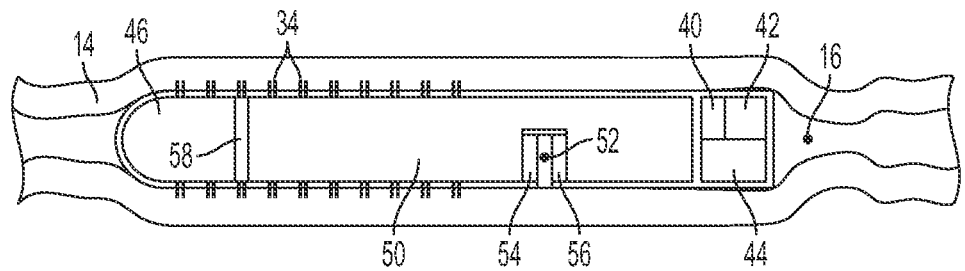
FIG. 7 is a section view, illustrating the device of FIG. 6 dispensing a drug by gas-volume displacement.

In some embodiments, an expandable component my be provided within the housing to cause dispensing of the drug when the expandable component expands. For example, as illustrated in FIGS. 6 and 7, an internal gas-volume displacement pump may be provided in or adjacent to a pump reservoir 50 to actuate the dispensing of the drug contained in drug repository 46 via a positive displacement process. In one embodiment, the pump may include a cathode 54 and anode 56 which contact water or an aqueous solution inside the pump reservoir 50. A channel 52 may be provided in housing to allow aqueous secretions from the mucosal tissue 14 to fill the channel 52 and contact the cathode 54 and anode 56. In other embodiments, a channel 52 that is in fluid communication with the interior space of the lumen may be omitted and electrolytes may be provided on board the device. For example, the pump reservoir 50 may comprise an ionic solution such as sodium chloride. Alternatively, the pump reservoir 50 may contain deionized water, and a solid electrolyte may be provided in place of the channel 52 so that the solid electrolyte contacts the surfaces of the cathode 54 and anode 56 facing the channel 52. The controller 42 may be configured to control the timing and sequence of delivery of the drug by applying electrical potentials to the cathode 54 and anode 56. A mechanism for generating a gas inside the pump reservoir 50 using the cathode 54 and anode 56 is described in greater detail hereinafter.

Figure 8:
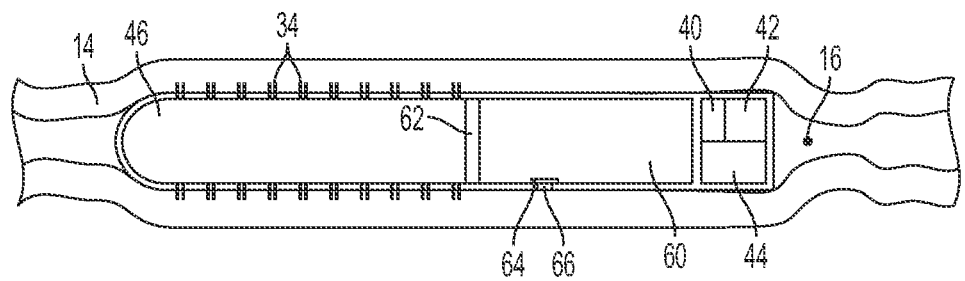
FIG. 8 is a section view, illustrating a drug delivery device having a component enlargement mechanism for dispensing a drug through microneedles.
Figure 9:
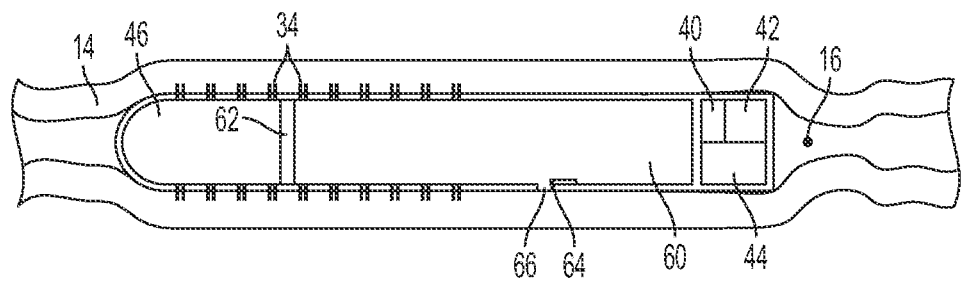
FIG. 9 is a section view, illustrating the device of FIG. 8 dispensing a drug by internal component enlargement.

In other embodiments, the expandable component may comprise a swellable material or an expandable reservoir. For example, as illustrated in FIGS. 8 and 9, a swellable material or expandable reservoir 60 may be provided in the housing. A valve 64 may be actuated to allow the ingress of water into the housing via a port 66. In certain embodiments, the expanding component may be a swellable matrix or gel. In other embodiments, the expandable reservoir may contain a phase-transformable material that may change phase from solid or liquid to gas when heat or an electromagnetic field is applied to the material. The controller 42 may be configured to control the timing and sequence of delivery of the drug by actuating a heating source or an electromagnetic field. As is described in greater detail below, various other actuator mechanisms may be used to dispense the drug from the housing via a positive displacement process.

A. Housing

The housing may be generally configured to facilitate deployment of the drug delivery device within a mucosal lumen. In some embodiments, the device may be placed within the lumen by insertion into the lumen via an exterior body orifice. Accordingly, in some embodiments, the housing is shaped and dimensioned to allow insertion and placement of the device within the intended lumen via the exterior body orifice. Specifically, the housing may be shaped and dimensioned for vaginal, cervical, uterine, or rectal insertion and placement. The materials of construction, size, shape, and surface features and other characteristics of the device housing are configured so that the device can be deployed into the mucosal lumen, retained securely in the lumen during operation of the device, and generally retrieved from the lumen following operation of the device or when otherwise desired to be removed. The device configuration is based upon the particular lumenal site and human or animal anatomical considerations, for deployment with minimal discomfort to the patient.

The housing may contain dispensers for dispensing one or more drugs and a control module for controlling the release and delivery of the drugs. The dispensers may include one or more repositories disposed therewithin for containing one or more drugs and microneedles for dispensing the one or more drugs therethrough. The microneedles may extend, or be extendable from, the housing. The housing may also contain actuators for moving the microneedles from a first position to a second position. The actuator may also be controlled by the control module.

The housing may be formed of any biocompatible material. Moreover, the housing material may be resistant to degradation in the environment of the lumen. Examples of suitable materials include stainless steel, titanium, and certain polymers. The material forming the housing may include a coating to enhance biocompatibility and/or operation of the device.

B. Microneedles

The device includes a plurality of microneedles for penetrating the mucosal tissue at a selected time after the device has been deployed into the lumen. As used herein, the term "microneedle" refers to microneedles, microblades, and other microprojections known in the art. The microneedle may be solid or hollow. It may have one or more axial bores or channels, and/or one or more grooves, and/or one or more lateral apertures, as known in the art to facilitate fluid flow through or around the microneedle. The microneedle may have a straight or tapered shaft, or it may have both an untapered base portion and a tapered end portion. The microneedles can be formed with shafts that have a circular or non-circular lateral cross-section The microneedle may have a pyramidal shape, with a square or triangular base. The tip portion of the microneedles can have a variety of configurations. The tip of the microneedle can be symmetrical or asymmetrical about the longitudinal axis of the shaft. The tips may be beveled, tapered, squared-off, or rounded. In various embodiments, the microneedle may have a length of about 10 µm to about 1500 µm, such as about 50 µm to about 1400 µm, about 150 µm to about 1300 µm, about 300 µm to about 1300 µm, about 300 µm to about 1000 µm, or about 300 to about 800 µm. In various embodiments, the base portion of the microneedle has a maximum width or cross-sectional dimension of about 10 µm to about 500 µm, about 50 µm to about 400 µm, or about 100 µm to about 250 µm. For a hollow microneedle, the maximum outer diameter or width may be about 50 µm to about 400 µm, with an aperture diameter of about 5 µm to about 100 µm. The microneedle may be fabricated to have an aspect ratio (width:length) of about 1:1 to about 1:10. Other lengths, widths, and aspect ratios are envisioned. The microneedles may be fabricated using methods and materials known in the art, including but not limited to biocompatible metals and polymers.

The term "at a selected time," when used to refer to the time the microneedles penetrate the mucosal tissue after the device has been deployed into the lumen, means that the plurality of microneedles penetrate the mucosal tissue after the device is deployed within the lumen for a period of time. This feature may allow the device to be positioned in a desired orientation or location within the lumen before the microneedles penetrate the mucosal tissue and inhibit positional adjustment of the device. For example, the device may be placed at a specific location in the lumen in a specific orientation with respect to the lumen and time may be allowed for the mucosal tissue to frictionally engage and maintain the device in the designated location and orientation prior to penetrating the mucosal tissue with the microneedles.

Various mechanisms may be used to control the timing of mucosal tissue penetration. In some embodiments, moveable microneedles may be actuated to extend from the housing into the mucosal tissue. In other embodiments, static microneedles may be used in combination with a dissolvable coating or moveable covering. The dissolvable coating or moveable covering may expose the microneedles to the mucosal tissue at a selected time after the device is deployed into the lumen.

As illustrated in FIGS. 1 and 2, a plurality of moveable microneedles 26 may be provided on a microneedle carriage 24 to allow the microneedles 26 to be moveable in unison. An actuator 28, which may be a linear actuator, may actuate the movement of the microneedles 26 and microneedle carriage 24 from a first position (FIG. 1) to a second position (FIG. 2) in which the microneedles 26 penetrate the mucosal tissue 14. As illustrated in FIG. 1, the microneedles 26 may be entirely contained within the housing 12 when the device 10 is initially deployed in the lumen 16. The actuator 28 may also actuate the movement of the microneedles 26 and microneedle carriage 24 from the second position (FIG. 2) to the first position (FIG. 1).

In some embodiments, the microneedles 26 may penetrate the mucosal tissue 14 and then may be withdrawn back into the housing 33 leaving disruptions in the mucosal tissue 14. The device may thereafter dispense the drug through holes in the housing 10 (for example, the holes in the housing 10 through which the moveable microneedles 26 extend when moving between the first position and the second position) onto the portion of the mucosal tissue disrupted by the needles. The disruptions may facilitate the transmucosal delivery of the drug.

As illustrated in FIGS. 3 and 4, a plurality of static microneedles 34 may extend from the surface of the housing 33 of the device 31. The static microneedles 34 may be at least partly covered by a dissolvable coating 32. As illustrated in FIG. 2, the microneedles 34 may penetrate the mucosal tissue 14 as the dissolvable coating 32 dissolves. The dissolvable coating may comprise a sugar or other water-soluble material that will dissolve in the lumen 16. The material and thickness of the coating 32 may be varied to control the length of time that the device may be deployed in the lumen 16 before the microneedles 34 may penetrate the mucosal tissue 14. A moveable covering may be employed to expose the microneedles at a selected time to achieve a similar effect. The housing may comprise components that move to uncover the microneedles 34 or move to allow the mucosal tissue 14 to contact the microneedles 34 at a selected time. For example, the moveable component may move radially inward toward the base of the static microneedles 32 and the housing 33, mimicking the dissolution of a dissolvable coating. An actuator may be employed to actuate the movement of the moveable covering.

To facilitate removal of the device from the lumen, the microneedles may be withdrawn from the mucosal tissue. For example, the moveable microneedles may be actuated to be withdrawn into the housing of the device. Alternatively, the microneedles may be dissolvable, biodegradable or bioerodible such that after a period of time the microneedles dissolve, degrade or erode in the mucosal tissue or lumen. The microneedles may dissolve passively or actively. For example, the microneedle may comprise a metal that forms a soluble salt when a voltage is applied to the metal and the metal is in contact with an ionic species. In this example, the microneedle may be actively dissolved by the application of a voltage to the microneedle after the drug is dispensed.

The microneedles may be formed in various shapes or structures. Each of the microneedles may have a conduit or channel that is fluidly connected to the drug repository to allow the drug to flow freely from the drug repository into the mucosal tissue via the conduit or channel. Alternatively, the microneedle may comprise a porous material and the drug may be delivered into the mucosal tissue through the pores of the microneedle. In other embodiments, nonporous, non-channeled microneedles (e.g., microneedle pins) may be used to create disruptions in the mucosal tissue. The microneedles may be formed in various shapes including, but not limited to, cylindrical, pyramidal, and conical. The tip of the microneedle may include a bevel or other feature to facilitate penetrate of the mucosal tissue. When extended from the housing or exposed, the microneedles may extend from the outer surface of the housing a length of about 10 µm to about 1000 µm, and more preferably about 150 µm to about 450 µm.

The microneedles may be formed of various materials. For example, the microneedles may be made of a metal/alloy such as stainless steel, aluminum/aluminum alloy, nickel/nickel alloy, or titanium/titanium alloy. The microneedles may also be formed of various polymeric materials, including biodegradable polymers. Various methods are known for producing metal and polymeric microstructures, such as microneedles, including micro-molding and etching processes.

C. Drug Dispenser

A drug dispenser may be provided for actively dispensing the drug from the drug delivery device by positive displacement. The drug may be stored in the device in a repository and dispensed from the housing into the lumen or mucosal tissue at a selected time. The drug dispenser may be arranged to dispense the drug from the housing to a region of the mucosal barrier disrupted by the microneedles or through the microneedles into the mucosal tissue.

In some embodiments, the drug may be released from the housing via passive diffusion. In other embodiments, the drug dispenser may employ various positive displacement elements for dispensing the drug from the device including mechanical displacement, osmotic swelling displacement, gas-volume displacement, electrostatically-induced compression, piezoelectric actuation, or a thermally/magnetically induced phase transformation. The positive displacement element may comprise an actuatable dispensing valve in combination with a static pressure head. The term "positive displacement," as used herein, generally refers to any process whereby the drug is dispensed from the drug delivery device under force provided from within the drug delivery device. Accordingly, the term "positive displacement" does not refer to the passive, chemical diffusion of the drug out of the device.

In some embodiments, the drug is stored within a repository within the housing, and is actively dispensed from the housing through a plurality of microneedles by a mechanical displacement element such as a piston or spring. For example, in the embodiment of FIGS. 4 and 5, the integral control module 40 may selectively transmit electrical or mechanical power to the actuator 38, advancing the piston 36 of the actuator 38 through the drug repository 46 and dispensing the drug through the microneedles 34. The actuator 38 may be, for example, a linear actuator.

In some embodiments, the drug is dispensed by gas-volume displacement. For example, as illustrated in FIGS. 6 and 7, the device may include a pump reservoir 50 containing water or an aqueous solution. A pair of electrodes (a cathode 54 and an anode 56) may be provided within the pump reservoir 50 for generating a gas, such as oxygen and hydrogen. A passage 52 may be provided between the electrodes to allow water from within the lumen 16 to exchange protons and electrons with the water or aqueous solution within the pump reservoir 50. In other embodiments, a channel 52 that is in fluid communication with the interior space of the lumen may be omitted and electrolytes may be provided on board the device. For example, the pump reservoir 50 may comprise an ionic solution such as sodium chloride. Alternatively, the pump reservoir 50 may contain deionized water, and a solid electrolyte may be provided in place of the channel 52 so that the solid electrolyte contacts the surfaces of the cathode 54 and anode 56 facing the channel 52.

An electrical potential of about 1.0 V or greater may be applied to the electrodes to generate $O_2$ at the anode. The reaction at the anode is described by EQ. 1. In the water, at the negatively charged cathode, a reduction reaction takes place, with electrons from the cathode being given to the hydrogen cations to form hydrogen gas as shown in EQ. 2. The pressure exerted by the generated oxygen and hydrogen causes piston 58 to advance into the drug repository 46, thereby causing the drug to dispense through the microneedles 34 into the mucosal tissue 14. The production of oxygen and hydrogen may be controlled by an integral control module 40 that is provided on-board the device in the housing. The control module 40 may include a power source 44, such as a battery, and a controller 42 that is programmed to supply the electrical potential to the cathode 54 and the anode 56 at a selected time.

Other positive displacement elements may be better understood with reference to FIGS. 8 and 9. In these examples, a drug contained in a drug repository 46 is dispensed by the enlargement of component 60. Component 60 may be, for example, a swellable material (such as a swellable gel) or an expandable reservoir. In some embodiments, the drug is dispensed by osmotic swelling displacement. Optionally, a valve 64 may be provided to selectively control the ingress of water into the repository or swellable material through a port 66 or a semi-permeable membrane. Water from the lumen 16 may be drawn into a repository or swellable material, causing the repository or swellable material to expand in volume. The expansion of the reservoir or swellable material may displace a volume of drug contained within the housing, causing the drug to be dispensed from the device into the mucosal tissue 14. The actuation of the valve 64 may be controlled by the integral control module 40.

In other embodiments, the drug may be dispensed by an expansive force supplied by an induced phase transformation. For example, component 60 may comprise an expandable reservoir containing a phase-transformable material. The phase-transformable material may be any liquid or solid that will undergo a phase transition from solid or liquid to gas when heated or subjected to an electro-magnetic field. When the material transforms to a gas, the material expands and advances through the drug repository 46 to dispense the drug from the device. The actuation of the phase-transformation may be controlled by the on-board control module 40.

In other embodiments, the drug may be positively displaced and dispensed from the housing by electrostatically-induced compression or using a piezoelectric actuator. For example, a dielectric elastomeric actuator or piezoelectric actuator may be arranged such that a change in voltage or current to the actuator causes the actuator to exert a compressive force on the drug in the drug repository. This compressive force may cause the drug to be dispensed from the device. The actuation of the actuator may be controlled by the on-board control module.

In other embodiments, positive displacement of the drug may be achieved using a static pressure head and an actuatable valve. The valve may be operated, for example, in an analog mode for amplitude-modulated dosing or it may be operated in a digital mode for frequency/duty-cycle modulated dosing. The static head pressure may be provided by loading the drug into the device under pressure or a the device may be pressurized after the drug is loaded in the device.

In various embodiments, the device may be configured for wireless operation, e.g., following deployment in the human or animal subject. In such cases, the device includes appropriate telemetry components as known in the art. For example, actuation of the microneedles positioning and/or the drug dispensing may be done from a remote controller, e.g., external to the human or animal subject. Generally, the telemetry (i.e. the transmitting and receiving) is accomplished using a first coil to inductively couple electromagnetic energy to a matching/corresponding second coil. The means of doing this are well established, with various modulation schemes such as amplitude or frequency modulation used to transmit the data on a carrier frequency. The choice of the carrier frequency and modulation scheme will depend on the location of the device and the bandwidth required, among other factors. Other data telemetry systems known in the art also may be used. In another case, the device is configured to be remotely powered, or charged. For example, the device may include a transducer for receiving energy wirelessly transmitted to the device, circuitry for directing or converting the received power into a form that can be used or stored, and if $$2H_2O(l) \rightarrow O_2(g) + 4H^+(aq) + 4e^-  \qquad \text{EQ. 1}$$

$$2H^+(aq) + 2e^- \rightarrow H_2(g) \qquad \text{EQ. 2}$$

stored, a storage device, such as a rechargeable battery or capacitor. In still another case, the device is both wirelessly powered and wirelessly controlled.

D. Drugs

Various drugs may be administered from the drug delivery device. The drug may be a protein or a peptide. For example, in some embodiments, the drug delivery device may be used to administer hormones or steroids, including, but not limited to, follicle stimulating hormone, parathyroid hormone, luteinizing hormone, gonadotropin-releasing hormone (GnRH), estradiol, progesterone, melatonin, serotonin, thyroxine, triiodothyronine, epinephrine, norepinephrine, dopamine, antimullerian hormone, adiponectin, adrenocorticotropic hormone, angiotensinogen, angiotensin, antidiuretic hormone, atrial-natriuretic peptide, calcitonin, cholecystokinin, corticotropin-releasing hormone, erythropoietin, gastrin, ghrelin, glucagon, growth hormone-releasing hormone, human chorionic gonadotropin, human placental lactogen, growth hormone, inhibin, insulin, insulin-like growth factor, leptin, melanocyte stimulating hormone, orexin, oxytocin, prolactin, relaxin, secretin, somatostatin, thrombopoietin, thyroid-stimulating hormone, thyrotropin-releasing hormone, cortisol, aldosterone, testosterone, dehydroepiandrosterone, androstenedione, dihydrotestosterone, estrone, estriol, calcitriol, calcidiol, prostaglandins, leukotrienes, prostacyclin, thromboxane, prolactin releasing hormone, lipotropin, brain natriuretic peptide, neuropeptide Y, histamine, endothelin, enkephalin, renin, and pancreatic polypeptide.

In some embodiments, the drug delivery device may be used to administer cytokine signaling molecules or immunomodulating agents that are used in cellular communication. These molecules commonly comprise proteins, peptides, or glycoproteins. Cytokine signaling molecules include, for example, the four a-helix bundle family which include the IL-2 subfamily (e.g., erythropoietin (EPO) and thrombopoietin (THPO)), the interferon (IFN) subfamily and the IL-10 subfamily. Cytokine signaling molecules also include the IL-1, IL-18 and IL-17 families In some embodiments, the drug delivery device may be used to administer drugs for pain management, including, but not limited to, corticosteroids, opioids, antidepressants, anticonvulsants (antiseizure medications), non-steroidal anti-inflammatory drugs, COX2 inhibitors (e.g., rofecoxib and celecoxib), tricyclic antidepressants (e.g., amitriptyline), carbamazepine, gabapentin and pregabalin, codeine, oxycodone, hydrocodone, diamorphine, and pethidine.

In some embodiments, the drug delivery device may be used to administer cardiovascular drugs. Examples of cardiovascular drugs that may be administered with the device include B-type natriuretic peptide (BNP), atrial natriuretic peptide (ANP), atrial natriuretic factor (ANF), atrial natriuretic hormone (ANH), and atriopeptin. Cardiovascular drugs that may be administered by the device also include, for example, antiarrhythmic agents, such as Type I (sodium channel blockers), including quinidine, lidocaine, phenytoin, propafenone; Type II (beta blockers), including metoprolol; Type III (potassium channel blockers), including amiodarone, dofetilide, sotalol; Type IV (slow calcium channel blockers), including diltiazem, verapamil; Type V (cardiac glycosides), including adenosine and digoxin. Other cardiovascular drugs that may be administered by the device include ACE inhibitors, such as, for example, captopril, enalapril, perindopril, ramipril; angiotensin II receptor antagonists, such as, for example, candesartan, eprosartan, irbesartan, losartan, telmisartan, valsartan; beta blocker; and calcium channel blocker.

E. Control Module

A control module is provided for controlling the actuation of the microneedles and/or the delivery of the drug into the mucosal tissue. The control module may be provided on-board the drug delivery device in the housing. The control module may include a power source and a controller. The power source may be any source of mechanical or electrical power, such as a battery or fuel cell. The controller may be programmable or it may be pre-programmed to deliver the drug in accordance and/or actuate the microneedles with a pre-designated schedule.

In some embodiments, the control module may further comprise one or more sensors for analyzing the environment around the device or within the lumen. For example, a sensor may be employed to detect the presence of a hormone or other substance in the lumen.

In some embodiments, the control module may further comprise a wireless receiver for receiving wireless control signals from a separate, detached transmitting device. In certain embodiments, the device may be deployed into the lumen by the patient or a physician, and, thereafter, the patient or physician may actuate the release of the drug using the transmitting device to transmit control signals to the placed device. Furthermore, in some embodiments, the control module receiver and transmitting device may both be transceivers capable of transmitting and receiving control signals and other communications from each other. Accordingly, in certain embodiments, the control module transceiver may transmit data relevant to the operation of the device, such as data regarding the dosages already administered, the dosing schedule, the level of drug remaining in the repositories, and the remaining battery charge, as well as data relevant to the environment of the lumen, such as data detected or measured by an integral sensor. In some embodiments, the control module may also be wirelessly powered.

F. Methods

Methods are provided for transmucosal drug delivery using intralumenal devices. The method includes placing the drug delivery device within the lumen of a patient. The patient may be a human or other mammalian animal (e.g., cow, horse, pig, or dog). The methods include various medical and veterinary therapies, as well as animal husbandry applications. The lumen may be, for example, a vagina, cervix, uterus, bladder, or rectum. The device may be adapted to contact essentially any mucosal tissue surface. The device may be placed in the lumen by inserting the device through an exterior orifice of the patient into the lumen. In some embodiments, the device may be in a form that may be orally administered for delivery of a drug via the mucosal tissue of the gastrointestinal tract.

After the drug delivery device is placed in the lumen, the microneedles of the drug delivery device may penetrate the mucosal side wall. In some embodiments, the microneedles may be actuated to penetrate the mucosal side wall by an integral control module at a selected time. The drug delivery device may then dispense the drug to a region of the mucosal tissue disrupted by the microneedles or through the microneedles into the mucosal tissue. The release of the drug from the device may also be actuated by the control module at another selected time after the microneedles have penetrated the mucosal tissue.

As illustrated in FIG. 1, the transmucosal drug delivery device 10 may be placed in a lumen 16. The drug delivery device 10 may be held in place by frictional engagement between the mucosal tissue 14 and the housing 12. As illustrated in FIG. 2, the microneedles 26 may then be actuated to extend from the housing 12 into the mucosal tissue 14 via actuation of the actuator 28. The actuation of the actuator 28 may be controlled by the control module 18.

Alternatively, as illustrated in FIGS. 3 and 4, a drug delivery device may be placed in the lumen 16, and a dissolvable coating 32 may be allowed to dissolve causing a plurality of static microneedles 34 to penetrate the mucosal tissue 14. Similarly, a moveable covering may be provided to expose the microneedles at a selected time. The moveable covering may be actuated by an on-board control module.

After the microneedles penetrate the mucosal tissue 14, the control module 40 may actuate the delivery of the drug. In the example of FIGS. 4 and 5, the control module 40 may supply electrical or mechanical energy to actuator 38. In the example of FIGS. 6 and 7, the control module may apply an electrical potential to the cathode 54 and the anode 56. As illustrated in FIG. 7, as gas is generated within the pump reservoir 50, the piston 58 advances through the drug repository 46, causing the drug to be dispensed through the microneedles 34. The device may thereafter be removed from the lumen. To facilitate removal, the microneedles may be biodegradable (in the case of static microneedles), or extendable microneedles may be actuated to be drawn back into the housing.

With reference to FIGS. 8 and 9, in embodiments in which a swellable material or enlargeable repository is used, the valve 64 may then be actuated to allow the ingress of water into the swellable material or expandable reservoir 60. Alternatively, the control module 40 may actuate the inducement of a phase change of a material in the expandable reservoir 60. For example, the control module 40 may actuate a heating element to heat the phase change material or may actuate a circuit that generates an electro-magnetic field. As illustrated in FIG. 9, the enlargement of the swellable material or expandable reservoir 60 forces the drug out of the microneedles 34 and into the mucosal tissue 14.

Applications

The drug delivery device and method may be used for various therapeutic applications. In some embodiments, the drug delivery device may be used to treat infertility in a female subject. For example, the drug delivery device may be placed in the vagina (or uterus, or other part of the birth canal) of a female subject. The microneedles may then penetrate the mucosal tissue. Thereafter, the drug delivery device may deliver follicle stimulating hormone to induce ovulation in the female subject. In some embodiments, the drug delivery device may be configured to deliver a plurality of hormones, including follicle stimulating hormone, luteinizing hormone, gonadotropin-releasing hormone separately, or in combination, in appropriate sequences, at appropriate times, and in appropriate amounts to treat infertility. The device may also dispense estradiol to regulate natural hormone production in the female subject. The appropriate dosing schedule and amounts may be determined by one in the field of reproductive pharmacology.

In another embodiment, the drug delivery device may be use to treat insulin dependent diabetes (Type I diabetes) in a subject. The drug delivery device may be placed within a lumen of the subject. The microneedles may then penetrate the mucosal tissue. Thereafter, the drug delivery device may deliver insulin (Humulin R, Novolin R), insulin isophane (Humulin N, Novolin N), insulin lispro (Humalog), insulin aspart (NovoLog), insulin glargine (Lantus) or insulin detemir (Levemir) to the patient at a selected time or times.

In another embodiment, the drug delivery device may be use to treat diabetes mellitus (Type II diabetes) in a subject. The drug delivery device may be placed within a lumen of the subject. The microneedles may then penetrate the mucosal tissue. Thereafter, the drug delivery device may deliver exenatide to the patient at a selected time or times.

In another embodiment, the drug delivery device may be use to treat breast or ovarian cancer in a subject. The drug delivery device may be placed within a lumen of the subject, such as the vagina for a female subject. The microneedles may then penetrate the mucosal tissue. Thereafter, the drug delivery device may deliver abraxane (or other drug having therapeutic effectiveness for treating breast cancer) to the patient at a selected time or times.

In another embodiment, the drug delivery device may be use to treat HIV/AIDS in a subject. The drug delivery device may be placed within a lumen of the subject. The microneedles may then penetrate the mucosal tissue. Thereafter, the drug delivery device may deliver Abacavir (ABC) or Cidofovir (or other drug having therapeutic effectiveness for treating HIV/AIDS) to the patient at a selected time or times. The device also may be used to treat other sexually transmitted diseases.

In another embodiment, the drug delivery device may be use to treat genital herpes in a subject. The drug delivery device may be placed within a lumen of the subject, such as within the vagina of a female subject. The microneedles may then penetrate the mucosal tissue. Thereafter, the drug delivery device may deliver acyclovir, famciclovir, or valacyclovir (or other drug having therapeutic effectiveness for treating genital herpes) to the patient at a selected time or times.

In another embodiment, the drug delivery device may be use to treat diabetes insipidus in a subject. The drug delivery device may be placed within a lumen of the subject. The microneedles may then penetrate the mucosal tissue. Thereafter, the drug delivery device may deliver desmopressin (or other drug having therapeutic effectiveness for treating diabetes insipidus) to the patient at a selected time or times.

In another embodiment, the drug delivery device may be use to treat osteoporosis in a subject. The drug delivery device may be placed within a lumen of the subject, such as within the vagina of a female subject. The microneedles may then penetrate the mucosal tissue. Thereafter, the drug delivery device may deliver ibandronate, calcitonin, or parathyroid hormone (or other drug having therapeutic effectiveness for treating osteoporosis) to the patient at a selected time or times.

It will be appreciated that various of the above-disclosed and other feature and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

We claim:

1. An intravaginal device for transmucosal drug delivery comprising:
    a housing shaped and dimensioned for intravaginal deployment and for holding the device in place in the vagina by frictional engagement between the housing and mucosal tissue of a human or animal subject;
    a drug-dispensing portion which contains at least one drug disposed in the housing;
    a plurality of solid microneedles extending, or being extendable from, the housing, the plurality of microneedles being configured to disrupt at least one region of a mucosal barrier adjacent the housing at a selected time after being intralumenally deployed in the human or animal subject; and a control module comprising a power source and a controller, the controller being configured to actuate release of the at least one drug from the housing after the plurality of solid microneedles penetrate the mucosal barrier, wherein the device is operable to dispense the drug from the housing to a region of the mucosal barrier disrupted by the plurality of solid microneedles.

2. The device of claim 1, wherein the drug comprises a protein or peptide.

3. The device of claim 1, wherein the drug comprises a hormone or steroid.

4. The device of claim 1, further comprising a receiver adapted to receive power or control signals from a transmitting device when the device is intralumenally deployed in the human or animal subject.

5. The device of claim 1, wherein the drug dispensing portion comprises a positive displacement element for actively dispensing the drug from the housing, the positive displacement element being selected from the group consisting of a mechanical displacement element, an osmotic swelling displacement element, a gas-volume displacement element, a magnetically-induced phase transformation element, a thermally-induced phase transformation element, a piezoelectric actuator, an electrostatically-induced compression element, an actuatable dispensing valve with a static pressure head, and a combination thereof.

6. The device of claim 1, further comprising an actuator configured to move the plurality of solid microneedles from a first position to a second position in which the plurality of solid microneedles penetrate the mucosal barrier at the selected time.

7. The device of claim 6, wherein the solid microneedles are contained within the housing in the first position.

8. The device of claim 6, wherein a controller is configured to actuate the release of the at least one drug after the plurality of solid microneedles are actuated to the second position.

9. The device of claim 1, further comprising a dissolvable coating or a moveable covering configured to expose the solid microneedles at the selected time after deployment of the device.

10. The device of claim 9, wherein a controller is configured to actuate the release of the at least one drug after the plurality of solid microneedles are exposed.

11. A method for local transmucosal delivery of a drug to a human or animal subject comprising:
deploying a drug delivery device within a vagina of a human or animal subject, the drug delivery device comprising a housing shaped and dimensioned for intravaginal deployment and for holding the device in place in the vagina by frictional engagement between the housing and mucosal tissue, and a drug-dispensing portion contained within the housing;
penetrating the mucosal tissue with a plurality of solid microneedles that extend from, or are extendable from, the housing at a selected time after the drug delivery device is deployed in the lumen; and
dispensing a drug from the drug-dispensing portion through one or more openings in the housing to the region of the mucosal tissue that is disrupted by the microneedles.

12. The method of claim 11, wherein the drug comprises a protein or peptide.

13. The method of claim 11, wherein the drug is dispensed from the drug delivery device via a positive displacement process.

14. The method of claim 13, wherein the positive displacement process comprises mechanical displacement, osmotic swelling displacement, gas-volume displacement, magnetically-induced phase transformation, thermally-induced phase transformation, piezoelectric actuation, electrostatically-induced compression, static pressure head displacement through an actuatable dispensing valve, or a combination thereof.

15. The method of claim 11, wherein penetrating the mucosal tissue comprises moving a plurality of solid microneedles from a first position to a second position in which the plurality of solid microneedles penetrate the mucosal barrier.

16. The method of claim 11, wherein penetrating the mucosal tissue comprises dissolving a dissolvable coating or moving a moveable covering to expose the solid microneedles at the selected time after deployment of the device.

17. The method of claim 11, wherein after penetrating the mucosal tissue, the microneedles are withdrawn into the housing before the drug is dispensed from the housing.

18. An intravaginal device for transmucosal drug delivery comprising:
a cylindrical housing shaped and dimensioned for intravaginal deployment and for holding the device in place in the vagina by frictional engagement between the housing and mucosal tissue of a human or animal subject, the housing having an elongated sidewall disposed between opposed ends;
a plurality of microneedles extending from, or extendable from, the elongated sidewall of the housing, the microneedles being configured to penetrate a region of the mucosal barrier adjacent to the sidewall of the housing at a selected time after the device is intravaginally deployed in the human or animal subject, and
a drug dispenser comprising a drug repository containing at least one drug and a positive displacement element adapted to dispense the at least one drug from the elongated sidewall of the housing through the plurality of microneedles or onto the region of the mucosal tissue disrupted by the microneedles.

19. The device of claim 18, further comprising a controller configured to control the actuation of the positive displacement element.

20. The device of claim 18, wherein the positive displacement element is selected from the group consisting of a mechanical displacement element, an osmotic swelling displacement element, a gas-volume displacement element, a magnetically-induced phase transformation element, a thermally-induced phase transformation element, and a combination thereof.

21. The device of claim 18, wherein the drug comprises a protein or peptide.

22. The device of claim 18, further comprising an actuator configured to move the plurality of microneedles from a first position to a second position in which the plurality of microneedles penetrate the mucosal barrier at the selected time.

23. The device of claim 18, further comprising a dissolvable coating or a moveable covering configured to expose the microneedles at the selected time after deployment of the device.

24. The device of claim 18, wherein the sidewall comprises a plurality of openings configured to dispense the drug therethrough in at least two opposed directions from the sidewall.

25. The device of claim 18, wherein the microneedles are solid.

* * * * *